United States Patent [19]

Fossati

[11] Patent Number: 4,608,335
[45] Date of Patent: Aug. 26, 1986

[54] ENZYMATIC UREA ASSAY

[75] Inventor: Piero Fossati, Lissone, Italy

[73] Assignee: Miles Italiana S.p.A., Milan, Italy

[21] Appl. No.: 618,831

[22] Filed: Jun. 8, 1984

[30] Foreign Application Priority Data

Aug. 8, 1983 [IT] Italy ................. 48827 A/83

[51] Int. Cl.⁴ .................. C12Q 1/58; C12Q 1/48; C12Q 1/26
[52] U.S. Cl. ................................ 435/12; 435/15; 435/25
[58] Field of Search .................. 435/12, 15, 25

[56] References Cited

U.S. PATENT DOCUMENTS

| | | | |
|---|---|---|---|
| 3,655,516 | 4/1972 | Roon et al. | 435/12 |
| 4,059,407 | 11/1977 | Hochstrasser | 435/12 |
| 4,248,973 | 2/1981 | Kallies | 435/12 |

OTHER PUBLICATIONS

Colowick, et al., Methods in Enzymology, vol. I, (1955), pp. 482-486, Acedemic Press, Inc.
Tabor, et al., Methods in Enzymology, vol. XVIIB, (1971), pp. 741-746, Acedemic Press Inc.

Primary Examiner—Christine M. Nucker
Attorney, Agent, or Firm—Mary G. Boguslaski

[57] ABSTRACT

A composition, device and method useful as an enzymatic urea assay based on the use of urea amidolyase comprising urea amidolyase, pyruvate kinase, pyruvate oxidase, mono and divalent cations, phosphoenolpyruvate, thyamine pyrophosphate, ATP, bicarbonate, phosphate, a color indicator system and optionally inorganic phosphate, a buffer having a pH range of from about 6.5 to 9.5, and sodium or potassium ferrocyanide. After contacting the test solution or body fluid sample with the assay composition, reading can be accomplished visually or instrumentally.

20 Claims, No Drawings

ENZYMATIC UREA ASSAY

BACKGROUND OF THE INVENTION

1. Field of the Invention

The present invention relates generally to the field of diagnostic compositions and, more particularly, to diagnostic tests useful in the qualitative and quantitative determination of urea in fluids, especially blood and urine.

2. Description of the Prior Art

Urea is the major end product of protein metabolism in man and other mammals. This product is formed in the liver, passes into the blood and is excreted through the kidneys into the urine, where it constitutes the major fraction of organic substances present. An excess of blood urea, referred to as azotemia, almost invariably indicates impairment of renal function. The determination of blood urea (usually expressed as urea nitrogen in the United States) is one of the most routinely performed clinical chemistry tests. Urea "clearance", or removal of urea from the blood by the kidneys, can be determined by urine urea concentration and used as a measure of glomerular filtration rate.

Routine clinical chemistry methods used to determine urea concentration in biological fluids are classified as direct, through the condensation of urea with suitable reagents able to form a measurable chromogen, or indirect, through the determination of ammonia as a product of urease action on urea.

The direct method involving diacetylmonoxime, described in R. J. Henry, et al, Clinical Chemistry—Principles and Technics, Harper & Row, 2nd Edition (1974), has been widely applied in routine clinical chemistry, both with manual and automated procedures. This method suffers many disadvantages: nonspecificity due to interfering reactions with citrulline, allantoin, and other body fluid components; the need for daily preparation of a standard curve or two point calibration; rapid loss of color due to photosensitivity; and manipulative problems such as the high temperature required, odor and irritating fumes. For these reasons, the indirect enzymatic methods are generally preferred.

Indirect methods are based on enzymatic conversion of urea to ammonia by urease (urea amidohydrolase, EC 3.5.1.5), according to the reaction:

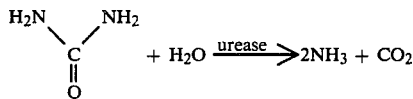

and subsequent determination of the liberated ammonia with suitable reagent system (R. Richterich, "Clinical Chemistry—Theory and Practice", translated from the 2nd German Edition, S. Karger, Basel (1969) and H. U. Bergmeyer, "Methods of Enzymatic Analysis", 2nd English Edition, Vol. 4, Verlag Chemie—Academic Press, New York (1974)). Specificity is the chief advantage of enzymatic methods since only urea is hydrolyzed by urease.

The most popular laboratory method is based on The Berthelot reaction in which ammonium ions react in alkaline medium with phenol and hypochlorite to give the blue dye indophenol. Urea determination by this method requires two steps: in the first step the sample is incubated at 37 degrees C. (usually from 10 to 20 minutes) with urease at the pH most suitable for the enzymatic reaction (i.e., around 6.5); in the second step alkaline solutions of phenol and hypochlorite are added and incubation is carried out for developing color, usually at 37 degrees C., from 10 to 30 minutes.

Another method is described in Bergmeyer, supra, which allows determination of ammonium ions derived from the enzymatic reaction with urease by the enzyme glutamate dehydrogenase (GlDH), according to the reaction:

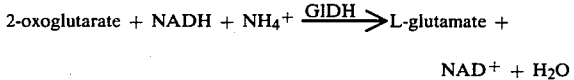

$$NAD^+ + H_2O$$

with measurement of the decrease in the reduced nicotinamide adenine dinucleotide (NADH) absorbance at 340 (or 334, or 366) nanometers (nm). Various changes have been made in this method in order to use it as a kinetic analysis with one step and one reagent preparation. In spite of these improvements, the use of this method in routine clinical chemistry remains limited because of the high cost of the reagents and lack of applicability to automated continuous-flow analyzers.

U.S. Pat. No. 4,194,063 describes a composition and method for the determination of urea in which the ammonia liberated from the urea by the action of urease is detected by condensation with a β-diketone in the presence of an aldehyde and the color produced is monitored spectrophotometrically or spectrofluorimetrically. Although a single-step procedure, this method requires either a long incubation period or high reaction temperatures to perform the assay in a reasonable time.

R. J. Roon and B. Lowenberg in "Methods in Enzymology", Colowick & Kaplan Ed., Academic Press, XVII, 317 (1970) described the preparation and properties of urea amidolyase (EC 3.5.1.45). The Roon method, designed to assay the activity of urea amidolyase preparations, involves the spectrophotometric determination of adenosine diphosphate (ADP) using phosphoenolpyruvate, pyruvate kinase and lactate dehydrogenase, monitoring the decrease in absorbance resulting from the oxidation of DPHN (syn. NADH). A urea assay carried out by Roon's pathway would give no advantage over current UV methods by glutamate dehydrogenase. In fact, due to the stoichiometry of the reactions involved, this pathway would have half the sensitivity of the glutamate dehydrogenase pathway.

U.S. Pat. No. 4,246,342, assigned to Toyo Jozo, discloses an analytical method for the determination of pyruvate and suggests that ADP may be determined by the pyruvate pathway if first reacted with phosphoenol pyruvate and pyruvate kinase to generate pyruvate.

It has been found that an enzymatic urea assay based on the use of urea amidolyase can be accomplished through a pathway allowing a sensitive colorimetric one-step assay which provides improved results over prior art methods utilizing urease.

SUMMARY OF THE PRESENT INVENTION

It is an object of the present invention to provide a reliable urea test which, as a single-step reaction with reading in the visible spectrum range, is convenient for routine use and adaptable to automated instruments. The use of urea amidolyase, pyruvate kinase, pyruvate oxidase, mono- and divalent cations, phosphoenolpyruvate, thiamine pyrophosphate, adenosine triphosphate, bicarbonate, a color indicator system and optionally inorganic phosphate, a buffer having a pH range of from about 6.5 to 9.5 and sodium or potassium ferrocyanide for detecting urea in a fluid sample is also an object of the present invention. A composition, device and method for the detection of urea in a fluid sample, including body fluids such as urine and blood (plasma or serum), are provided. The composition comprises urea amidolyase; pyruvate kinase; pyruvate oxidase; divalent cation, preferably $Mg^{++}$; monovalent cation, preferably $K^+$; phosphoenolpyruvate; thyamine pyrophosphate; adenosine triphosphate (ATP); and a bicarbonate to generate hydrogen peroxide and an indicator system; preferably peroxidase, 4-aminophenazone and a phenol or substituted phenol such as p-hydroxybenzenesulfonic acid or 2-hydroxyphenylacetic acid. Preferably the composition also includes inorganic phosphate.

Detection of the hydrogen peroxide can also be accomplished by employing "reversible" indicators such as o-dianisidine, tetramethylbenzidine, leucodyes, and the like. In any event, quantitation is accomplished colorimetrically by relating the color formation to the original urea concentration.

The composition can be provided in a "kit" format which can be reconstituted for use as a single working solution, preferably buffered at a pH from about 6.5 to about 9.5, or incorporated on a carrier to provide a test device, such as a tablet or reagent matrix.

The present invention combines several advantages making it suitable for routine use: (1) a single working reagent provides a convenient one-step reaction; (2) the visible range reading avoids expensive equipment required for ultraviolet readings; (3) the system avoids high temperature reaction; and (4) the procedure permits easy adaptation to automated instruments.

A fuller understanding of the invention will be attained by referring to the following description and claims.

DESCRIPTION OF THE PREFERRED EMBODIMENTS

The present invention is based on the use of urea amidolyase in an enzymatic assay for urea. The composition according to the present invention comprises enzymatic means responsive to the presence of urea in a fluid sample to produce hydrogen peroxide and a color indicator system responsive to hydrogen peroxide to produce a colorimetric response. The "urea responsive means" comprise urea amidolyase (E.C.3.5.1.45), pyruvate kinase (E.C.2.7.1.40) and pyruvate oxidase (E.C.1.2.3.3). Additionally, adenosine-5'-triphosphate (ATP), bicarbonate, cations, phosphoenolpyruvate (PEP), and thyamine pyrophosphate are required.

Preferably inorganic phosphate is added to the composition.

The reaction scheme is as follows:

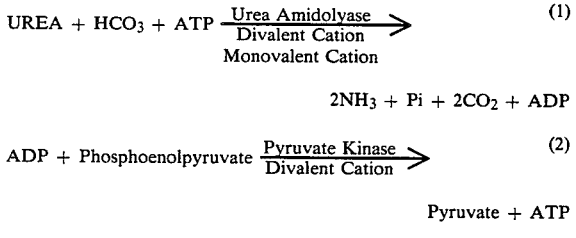

Acetylphosphate + $CO_2$ + $H_2O_2$ the hydrogen peroxide generated can then be determined with the use of a color indicator system.

Preferably, the color indicator system comprises peroxidase, 4-aminophenazone and phenol or a substituted phenol, such as 2-hydroxyphenylacetic acid, according to the following reaction:

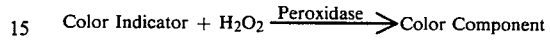

The color formed is proportional to the concentration of hydrogen peroxide and, consequently, to the concentration of urea. The concentration of urea can therefore be determined by a simple measurement of the absorbance of the reacted solution in the visible range, generally between 400 to 700 nm, with a colorimeter or a photometer.

Since the amount of color developed at any given time is proportional to the urea concentration, either and end-point method or a rate assay method can be used.

The enzyme urea amidolyase can be obtained from different microorganisms, see Biol. Chem., 274, 4107–4113 (1972). The other enzymes used are available commercially.

Divalent cations, $Mg^{++}$ or $Mn^{++}$ can be used, although $Mg^{++}$ is preferred. The monovalent cations can be chosen from the group $K^+$, $NH_4^+$, $Rb^+$ or $Cs^+$; $K^+$ is preferred.

Any adequately soluble bicarbonate, such as those of alkaline or alkaline-earth metals, can be used as source of bicarbonate ions. Sodium or potassium bicarbonate is preferred. Similar salts can be employed to supply an inorganic phosphate source.

The substances having peroxidative activity useful in the present invention can be chosen from various organic and inorganic sources. The various plant peroxidase, such as horseradish peroxidase or potato peroxidase, can be used. In addition, even though less satisfactory, hemin and hemin derivatives, hemoglobins and hematin can be used.

One suitable color indicator system couples the reaction of a peroxidatively active component, preferably peroxidase, and a color indicator component. Color indicator components useful with peroxidase include components useful with peroxidase include "reversible" indicators, e.g., o-dianisidine, tetramethylbenzidine, leuco-dyes, 2,2'-azine-di(ethylbenzothiazoline-6-sulfonic acid), syringaldazine, and the like; and oxidative couplers, such as 4-aminophenazone or its derivatives and a phenol or a naphthol, or an aromatic amine, or their derivatives; or 3-methylbenzothiazolinone hydrazone (MBTH) and a phenol, naphthol, or an aromatic amine or their derivatives.

Many appropriately substituted phenols, know in the art, can be used in the present invention. Examples of such substituted phenols are disclosed in Meittani, U.S. Pat. No. 3,886,045, now reissued as U.S. Pat. No. Re 29,498, incorporated herein by reference. The preferred substituted phenol is 2-hydroxyphenylacetic acid. In addition 2-, 3- and 4-hydroxybenzylalcohol, o-, m- and p-hydroxybenzenesulfonic acid; 4-chloro-3,5-methylphenol; and 2-hydroxy-5-chlorobenzenesulfonic acid can be used. Suitable naphthols are e.g., 1-naphthol, 2-naphthol, 3-hydroxy-2-naphthoic acid, and their sulfonated derivatives. Suitable aromatic amines are e.g., N,N-dimethyl- and N,N-diethyl-aniline; N,N-dimethyl-o-toluidine; N,N-dihydroxyethyl-o- or m-toluidine; and 3-N,N-dimethylaminobenzoic acid. All their soluble salts, such as sodium or potassium for phenols and naphthols, and hydrochlorides for amines, can be used.

Another suitable color indicator system utilizes catalase, by monitoring the formaldehyde generated in presence of methanol through the reaction with ammonium ions and a $\beta$-diketone to form dihydrolutidine derivatives or through the reaction with 4-amino-3-hydrazino-5-mercapto-1,2,4-triazole, or other products capable of condensing with formaldehyde to give color.

Finally, color can be generated without enzymes through the oxidation of metal organic complexes, such as e.g., titranium (IV)-4(2-pyridylazo)resorcinol; or titanium (IV)-xylenol orange.

Various alkali metal ferrocyanides such as potassium, sodium, and calcium ferrocyanide can be used to increase assay specificity by decreasing bilirubin interference in body fluid samples. Ammonium ferrocyanide and ferrocyanide generating compounds can also be used as sources of ferrocyanide.

The total process occurs in either base or acid buffered systems. Suitable buffers include phosphate, N-2-hydroxyethylpiperazine-N'-2-ethanesulfonic acid (HEPES), 3-(N-morpholino)propanesulfonic acid (MOPS), tris(hydroxymethyl)-aminomethane (TRIS), N-tris(hydroxymethyl)-methyl-2-aminoethanesulfonic acid (TES), N-2-hydroxyethylpiperazinepropanesulfonic acid (EPPS), diethanolamine and dimethyl glutarate.

Additional materials such as stabilizing agents and other conventional additives, can be employed if desired. The composition can be used in solution form prepared with solvents such as water, physiological solution, or organic solvents, such as methanol or mixtures thereof.

Workable concentration ranges and preferred concentration ranges are shown below:

|  | Workable | Preferred |
| --- | --- | --- |
| Urea amidolyase | 0.01–100 I.U./ml | 0.05–30 I.U./ml |
| Pyruvate kinase | 0.1–100 I.U./ml | 0.5–20 I.U./ml |
| Pyruvate oxidase | 0.1–10 I.U./ml | 0.2–5 I.U./ml |
| Peroxidase | 0.1–100 I.U./ml | 0.2–50 I.U./ml |
| Phosphoenolpyruvate | 0.1–10 mM | 0.2–5 mM |
| ATP | 0.1–10 mM | 0.2–5 mM |
| Bicarbonate | 0.1–50 mM | 1–20 mM |
| Thyamine pyrophosphate | 0.01–2 mM | 0.05–1 mM |
| Cation (divalent) | 0.1–20 mM | 1–10 mM |
| Cation (monovalent) | 0.1–10 mM | 0.5–5 mM |
| Phenol | 0.1–20 mM | 0.5–10 mM |
| 4-aminophenazone | 0.05–10 mM | 0.1–2 mM |
| Phosphate | 0–10 mM | 0.5–5 mM |
| Buffer | pH 6.5–9.5 | pH 6.8–8.0 |

Units: International Units per milliliter (I.U./ml); millimolar (mM).

The enzyme activity is expressed in international units (I.U.), one I.U. being the amount of enzyme activity required to catalyze the conversion of 1 micromole ($\mu$mol) of substrate per minute under specified conditions of pH and temperature.

The solution itself containing the composition according to the invention can be used to detect urea by adding it to a body fluid specimen such as urine, plasma, or serum. The reagents can be provided in a "kit" format, e.g., a series of bottles containing one or more of the above components, either in solution, or as a premixed powder, or as a lyophilized powder, which can be reconstituted for use as a single working solution. The kit can contain optionally a suitable urea standard.

The composition can be incorporated into a tablet taking the form of a pressed or molded tablet containing conventional carrier material or a carrier matrix to provide a dry test device. The term "carrier matrix", as used herein, refers to any means suitable for containing specified amounts of the composition.

The carrier matrix, accordingly, can comprise any substance capable of being incorporated with the ingredients. Thus, the matrix can take on many known forms, such as those utilized for reagent strips for solution analysis. For example, U.S. Pat. No. 3,846,247 teaches the use of felt, porous ceramic strips and woven or matted glass fibers. As substitutes for paper, U.S. Pat. No. 3,522,928 teaches the use of wood sticks, cloth, sponge material and argillaceous substances. The use of synthetic resin fleeces and glass fiber felts in place of paper is suggested in British Pat. No. 1,369,139. Another British Pat. No. 1,349,623, suggests the use of a light-permeable meshwork of thin filaments as a cover for an underlying paper matrix. This reference also suggests impregnating the meshwork with other potentially incompatible reagents. French Pat. No. 2,170,397 teaches the use of carrier matrices having greater than 50% polyamide fibers therein. Another approach to carrier matrices is disclosed in U.S. Pat. No. 4,046,513, wherein the concept of printing reagents onto a suitable carrier matrix is employed. U.S. Pat. No. 4,046,514 discloses the interweaving or knitting of filaments bearing reagents in a reactant system.

It is, therefore, to be appreciated that in producing a test device of the invention all such carrier matrix concepts can be employed, as can others. The matrix can include a system which physically entraps any or all of these ingredients, such as polymeric microcapsules which rupture upon contact with an aqueous solution. For example, one or more of the enzymes, or the means responsive to the oxidation product of the enzymes, can be maintained separately within the same carrier matrix as the composition, without interaction therewith until contacted with a solution. The matrix can also comprise a system wherein the composition ingredients are homogeneously combined in a fluid or semifluid state, which later hardens or sets, thereby entrapping the ingredients.

The presently preferred method, however, is to impregnate a bibulous matrix, e.g., filter paper, with the composition, followed by affixing the impregnated matrix to a support member. The impregnation can be accomplished merely by dipping one piece of filter paper into the composition. Drying can be accomplished by any means which will not deleteriously affect the impregnated composition, usually by means of an air oven. The dried paper can thereafter be cut and mounted on one end of a support member, for example, a rigid or semi-rigid polystyrene film strip. Mounting of the paper on the strip can be accomplished through the use of a double-faced adhesive tape, such as that commercially available from the 3M Company as DOUBLE STICK ®

The resulting test device is advantageously used by momentarily dipping it in a test sample or by otherwise introducing a test sample onto the carrier matrix, whereby a detectable change (e.g., color) results when urea is present. Since the characteristic color reaction that takes place is dependent on the concentration of the urea, quantitative detection is possible.

The following examples describe experiments which were performed in developing the present invention and which illustrate preferred embodiments thereof. While the examples serve to illustrate the invention, they are not to be interpreted as limiting its scope, which is defined solely by the claims appended hereto. One skilled in the art will be able to make such variations, substitutions and changes in the components of the composition and ingredients and reaction parameters as may seem desirable.

EXAMPLE

A composition for the determination of urea in a sample is prepared in solution according to the formulation of Table I. All the chemicals and enzymes are commercially available, except urea amidolyase; an active preparation of this enzyme is obtained by urea grown Candida Utilis ATCC #8205, as described by Roon, R. J. and Levenberg, B., in "Methods in Enzymology", Colowick and Kaplan Ed., Academic Press, XVII, 317, 1970, and has a specific activity of 0.2 Units/mg. of protein.

TABLE I

| COMPOSITION FOR UREA DETERMINATION | |
|---|---|
| HEPES Buffer pH 7.5 | 80 mM |
| Urea amidolyase | 1 IU/ml |
| Pyruvate kinase | 2 IU/ml |
| pyruvate oxidase | 0.6 IU/ml |
| Peroxidase (Horseradish) | 1 IU/ml |
| ATP | 0.6 mM |
| Phosphoenolpyruvate | 0.5 mM |
| $KHCO_3$ | 0.8 mM |
| Thyamine pyrophosphate | 0.2 mM |
| $K_2HPO_4$ | 1.0 mM |
| 2-hydroxyphenylacetic acid | 2.5 mM |
| 4-aminophenazone | 0.3 mM |
| $MgSO_4$ | 6.0 mM |

2.0 ml of the above reagent mixture is added to 0.02 ml of a sample containing urea and let stand at room temperature for 15 minutes. After this time the absorbance of the solution is measured at 500 nm. The absorbance of a reagent blank, constituting all the reagents in the table minus the sample, is substracted from the sample absorbance to give the true absorbance value.

The value of the sample is determined by comparing the results of those of a urea standard processed by the same procedure.

Data in Table II is obtained from experiments according to Reactions 2–4 on ADP solutions and shows the expected relationship of urea concentration to absorbance, assuming the stiochiometry of Reaction 1.

TABLE II

| AQUEOUS UREA SOLUTION ASSAY | |
|---|---|
| Urea mg/dl | Absorbance at 500 nM |
| 10 | 0.093 |
| 20 | 0.187 |
| 50 | 0.463 |
| 100 | 0.930 |
| 150 | 1.390 |
| 200 | 1.858 |

Although the invention is described with a certain degree of particularity, it is understood that the present disclosure is made by way of example and that numerous changes in the details can be made without departing from the scope of the invention.

What is claimed is:

1. A composition for the enzymatic determination of urea in a fluid sample, which composition comprises urea amidolyase, pyruvate kinase, pyruvate oxidase, a divalent cation, a monovalent cation, phosphoenolpyruvate, thyamine pyrophosphate, adenosine triphosphate, bicarbonate, and a color indicator system.

2. The composition of claim 1 wherein the composition additionally comprises inorganic phosphate.

3. The composition of claim 1 wherein the color indicator system is a peroxidatively active agent and a color indicator component.

4. The composition of claim 3 wherein the peroxidatively active agent is peroxidase.

5. The composition of claim 3 wherein the color indicator component is a reversible indicator.

6. The composition of claim 3 wherein the color indicator component is an oxidative coupler.

7. The composition of claim 6 wherein the oxidative coupler comprises 4-aminophenazone and a phenol, a naphthol, or an aromatic amine.

8. The composition of claim 1 and a buffer having a pH range of from about 6.5 to 9.5.

9. The composition of claim 1 and sodium or potassium ferrocyanide.

10. A test device for the determination of urea which device comprises an inert carrier incorporated with the composition of any one of claims 1–9.

11. A method of making the test device of claim 10 wherein the composition is incorporated with the carrier by impregnating the carrier with a solution of said composition, followed by drying the impregnated carrier.

12. A process for the determination of urea in a fluid sample which comprises contacting said sample with the composition of any one of claims 1–9 and observing any resultant color formed.

13. A process for the determination of urea in a fluid sample which comprises contacting said sample with the test device of claim 10 and observing any resultant color formed.

14. A composition for the enzymatic determination of urea in a fluid sample, which composition comprises urea amidolyase, pyruvate kinase, pyruvate oxidase, $MgSO_4$, $K_2HPO_4$, phosphoenolpyruvate, thiamine pyrophosphate, adenosine triphosphate and $KHCO_3$ to liberate hydrogen peroxide; peroxidase, 4-aminophenazone, and 2-hydroxyphenylacetic acid.

15. The composition of claim 14 and a buffer having a pH range of from about 6.5 to 9.9.

16. The composition of claim 14 and sodium or potassium ferrocyanide.

17. A device for the determination of urea which device comprises an inert carrier incorporated with the composition of any one of claims 14 to 16.

18. A method of making the test device of claim 17 wherein the composition is incorporated with the carrier by impregnating the carrier with a solution of said composition, followed by drying the impregnated carrier.

19. A process for the determination of urea in a fluid sample which comprises contacting said sample with the composition of any one of claims 14 to 16 and observing any resultant color formed.

20. A process for the determination of urea in a fluid sample which comprises contacting said sample with the test device of claim 17 and observing any resultant color formed.

* * * * *